United States Patent
Deardorff

(10) Patent No.: US 6,554,826 B1
(45) Date of Patent: Apr. 29, 2003

(54) ELECTRO-DYNAMIC PHASED ARRAY LENS FOR CONTROLLING ACOUSTIC WAVE PROPAGATION

(75) Inventor: Dana L. Deardorff, Emeryville, CA (US)

(73) Assignee: TxSonics-LTD (IL)

( * ) Notice: Subject to any disclaimer, the term of this patent is extended or adjusted under 35 U.S.C. 154(b) by 0 days.

(21) Appl. No.: 09/557,185

(22) Filed: Apr. 21, 2000

(51) Int. Cl.[7] .............................................. A61B 18/04
(52) U.S. Cl. ........................................ 606/27; 181/176
(58) Field of Search ................................. 600/459, 439, 600/463, 472, 437; 73/644, 642; 601/3; 606/1, 2, 4

(56) References Cited

U.S. PATENT DOCUMENTS

| | | | |
|---|---|---|---|
| 4,387,720 A | * 6/1983 | Miller | ......................... 600/472 |
| 4,858,597 A | 8/1989 | Kurtze et al. | |
| 4,865,042 A | 9/1989 | Umemura et al. | |
| 4,893,624 A | * 1/1990 | Lele | ............... 601/3 |
| 5,247,935 A | 9/1993 | Cline et al. | |
| 5,275,165 A | 1/1994 | Ettinger et al. | |
| 5,291,890 A | 3/1994 | Cline et al. | |
| 5,307,812 A | 5/1994 | Hardy et al. | |
| 5,323,779 A | 6/1994 | Hardy et al. | |
| 5,327,884 A | 7/1994 | Hardy et al. | |
| 5,368,031 A | 11/1994 | Cline et al. | |
| 5,368,032 A | 11/1994 | Cline et al. | |
| 5,443,068 A | 8/1995 | Cline et al. | |
| 5,477,736 A | 12/1995 | Lorraine | |
| 5,490,840 A | 2/1996 | Uzgiris et al. | |
| 5,520,188 A | 5/1996 | Hennige et al. | |
| 5,526,814 A | 6/1996 | Cline et al. | |
| 5,546,360 A | * 8/1996 | Deegan | ........................ 310/335 |
| 5,565,628 A | * 10/1996 | Lorraine | ...................... 73/642 |
| 5,590,657 A | 1/1997 | Cain et al. | |
| 5,711,300 A | 1/1998 | Schneider et al. | |
| 5,769,790 A | 6/1998 | Watkins et al. | |
| 5,834,687 A | * 11/1998 | Talbot et al. | ............... 600/459 |
| 5,873,845 A | 2/1999 | Cline et al. | |
| 5,931,785 A | * 8/1999 | Mason | ....................... 600/459 |

OTHER PUBLICATIONS

Charles A. Cain, et al., "Concentric–Ring and Sector–Vortex Phased–Array Applicators for Ultrasound Hyperthermia", IEEE Transactions on Microwave Theory and Techniques, MTT–34, pp. 542–551, 1986.

Todd Fjield, et al., "The Combined Concentric–Ring and Sector–Vortex Phased Array for MRI Guided Ultrasound Surgery", IEEE Transactions on Ultrasonics, Ferroelectircs and Frequency Control, vol. 44, No. 5, pp. 1157–1167, Sep. 1997.

Nathan McDannold, et al., "MRI Evaluation of Thermal Ablation of Tumors and Focused Ultrasound", JMRI vol. 8, No. 1, pp. 91–100, Jan./Feb. 1998.

Kullervo Hynynen et al., "Principles of MR–Guided Focused Ultrasound", Chapter 25, pp. 237–243.

Harvey E. Cline, Ph.D., et al., "Focused US System for MR Imaging–Guide Tumor Ablation", Radiology vol. 194, No. 3, pp. 731–738, Mar. 1995.

Todd Fjield, et al., "Low–Profile Lenses for Ultrasound Surgery", Phys. Med. Biol. 44, pp. 1803–1813, 1999.

* cited by examiner

Primary Examiner—Roy D. Gibson
Assistant Examiner—Peter J Vrettakos
(74) Attorney, Agent, or Firm—Bingham McCutchen LLP

(57) ABSTRACT

An electro-dynamic phased array acoustic lens having an array of cells, each of which may be separately controlled to alter characteristics of an incident acoustic wave. Because each cell of the acoustic lens controls the delay and amplitude of the acoustic wave passing through that cell, such an acoustic lens may be used in combination with a single-element transducer to control the characteristics of acoustic waves with a similar degree of control, or more, as that provided by a phased multi-element transducer array. The acoustic lens may also be used in combination with a multi-element transducer, such that all elements of the transducer may be fired at the same phase and amplitude. In other words, an ultrasonic wave that passes through a given cell of the acoustic lens is phase offset as determined by that cell. The acoustic lens may be used in an ultrasonic ablation system to control the ultrasonic waves used to ablate the tissue.

33 Claims, 3 Drawing Sheets

ELECTRO-DYNAMIC PHASED ARRAY LENS FOR CONTROLLING ACOUSTIC WAVE PROPAGATION

FIELD OF THE INVENTION

The present invention relates generally to lenses that affect or control characteristics of acoustic waves passing through the lenses and, more particularly, to a lens having an array of independently controllable cells for dynamically controlling propagation of acoustic waves passing through the cells. The lens may be suitable for many applications, including focused ultrasound systems for coagulation necrosis of tissue, such as tumors.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors, thereby obviating the need for invasive surgery. For this purpose, piezoelectric transducers driven by electric signals to produce ultrasonic energy have been suggested that may be positioned external to the patient, but in close proximity to the tissue to be ablated. The transducer typically includes a phased array of piezoelectric elements, which are geometrically shaped and positioned such that the ultrasonic energy is focused at a "focal zone" corresponding to a target tissue region within the patient. The transducer elements may be sequentially focused and activated at a number of focal zones in close proximity to one another. This series of sonications is used to cause coagulation necrosis of an entire tissue structure, such as a tumor, of a given size and shape.

For such purposes, a spherical cap transducer array, such as that disclosed in U.S. Pat. No. 4,865,042 issued to Umemura et al., which is incorporated herein by reference in its entirety, may be used. A spherical cap transducer array typically includes a plurality of concentric rings disposed on a curved surface having a radius of curvature defining a portion of a sphere. The concentric rings generally have equal surface areas and may also be divided circumferentially into a plurality of curved transducer elements or "sectors," creating a sector-vortex array. As will be appreciated by those skilled in the art, many other geometric transducer arrays (e.g., flat or linear) may also be employed in a focused ultrasound system. The transducer elements are generally simultaneously driven by radio frequency (RF) electrical signals at a single frequency offset in phase and amplitude. The phase and amplitude of the respective drive signals may be controlled so as to focus the emitted ultrasonic energy at a desired "focal distance," i.e., the distance from the transducer to the center of the focal zone, and provide a desired energy level in the target tissue region. Notably, such a phased array configuration allows for limited repositioning of the transducer focal zone, without mechanical movement of the transducer itself. Such phased-array transducers also require complex drive circuitry and external amplification hardware that precisely drive each element of the transducer at a certain phase and amplitude in order to generate ultrasonic waves of the proper shape and energy to obtain the appropriate focal zone.

The transducer may be mounted within a fluid-filled casing, such as a table including a chamber that is filled with degassed water or similar acoustically transmitting fluid. The transducer may be connected to a positioning system that moves the transducer within the chamber, and consequently mechanically adjusts the focal zone of the transducer. Alternatively, the positioning system may move the transducer in a horizontal plane perpendicular to the line of propagation, with the focal distance controlled electronically, or other combinations of mechanical and electronic positioning may be used. The top of the table includes a flexible membrane and a fluid-filled bag that may conform easily to the contours of a patient lying on the table. In addition, an imaging device, such as a magnetic resonance imaging (MRI) device, may be provided for monitoring the treatment of a patient.

A patient may be disposed on the table with water, ultrasonic conducting gel, and the like applied between the patient and the bag, thereby acoustically coupling the patient to the transducer. The transducer may be focused towards a target tissue region within a tissue structure, which may, for example, be a cancerous or benign tumor. The transducer may be activated for sufficient time to substantially necrose the target tissue region, e.g., for about ten seconds or more. The transducer may be deactivated, for example, for sufficient time to allow heat absorbed by the patient's tissue to dissipate, e.g., for about sixty seconds or more. The transducer may then be focused on another target tissue region, for example, adjacent to the target tissue region, and the process repeated until the entire target tissue structure is ablated.

The entire process, i.e., involving a series of sonications necessary to ablate a target tissue structure, may take several hours. As a result, the patient must lie motionless inside the MRI chamber for a long time, subjecting the patient to increased discomfort and possible claustrophobia. As it is, patients generally dislike being in the small MRI chamber, so there is a need to reduce the amount of time needed to ablate tissue, as well as to reduce the treatment time for general concerns such as increased medical costs and surgical risks.

Transducer arrays may be useful for medical imaging (diagnostic ultrasound), non-destructive evaluation (NDE) of materials, and ultrasound therapy devices (high-intensity focused ultrasound). These transducer arrays are composed of numerous transducer elements that are difficult and costly to fabricate and require complex drive circuitry and hardware to power each transducer element. The arrays must have complicated driving hardware in order to provide separate control of the amplitude and phase of the acoustic wave to each element of the transducer. Thus, there is a need for an improved system and method to control the acoustic energy applied to the tissue while doing so in a faster manner.

One approach to simplify control and/or focus of the acoustic energy is through the use of a lens. Extensive work and research have been conducted on so-called "acoustic lenses" for decades. Much of this work has focused on solid, mechanical lenses, which usually have been fabricated out of a plastic or wax material. Acoustic waves travel through the lens material at a significantly different speed than in the surrounding medium (usually water). Therefore, the lens material may change the propagational velocity of the acoustic wave as it passes through the lens. Thus, the shape and profile of the lens may be constructed to provide a fixed geometric focus of the incident acoustic waves.

However, in many applications there is a need to control or produce multiple acoustic sources and/or multiple focal ranges and angles of incidence. Although some control of the acoustic beam may be gained by mechanical motion of a fixed focus lens, this approach is typically slow and cumbersome and most applications demand the type of beam control provided by one or two dimensional transducer arrays, which have multiple transducer elements. The presence of multiple transducer elements creates the same problems discussed above of increased complexity, cost and time. Thus, there is a need to provide the benefits and beam control that a phased array transducer provides without its accompanying excessive cost and complexity.

Two previous patents disclose using a voltage dependent material to dynamically alter acoustic transmission through a lens: (1) U.S. Pat. No. 5,546,360, "Ultrasonic Transducer with Lens having Electrorheological Fluid Therein for Dynamically Focusing and Steering Ultrasound Energy," Peter Lorraine, 1995; and (2) U.S. Pat. No. 5,477,736, "Electrically Steered Acoustic Lens," Thierry Deegan, 1996. Both of these patents are expressly incorporated herein by reference in their entirety. However, neither of these patents proposes the use or design of a practical phased array lens that may be controlled in real-time to simulate the effect of a phased array transducer.

Thus, there is a need for an acoustic lens that provides the ability to direct and alter the acoustic waves that are transmitted though the lens with the same degree of control provided by a transducer phased array, but offers a significantly simpler and relatively inexpensive design.

SUMMARY OF THE INVENTION

The present invention is directed to an electro-dynamic, phased array acoustic lens, and methods of its use. In a preferred embodiment, the lens is provided with an array of cells, each of which is separately controlled to alter characteristics of an incident acoustic wave passing through the lens. By providing for each cell of the lens to independently control the delay and/or amplitude of the incident acoustic wave, the lens may be used in combination with a single-element transducer to control the characteristics of acoustic waves with a similar degree of control, or more so, as that provided by a phased multi-element transducer array. The acoustic lens of the present invention may also be used in combination with a multi-element transducer. In other words, an ultrasonic wave that passes through a given cell of the acoustic lens is phase offset as determined by that cell.

In accordance with one aspect of the invention, an electro-dynamic phased array acoustic lens having an array of cells is provided, wherein each cell may separately control a characteristic, such as, amplitude or delay, of an acoustic wave that passes through the respective cell.

In accordance with another aspect of the invention, an acoustic ablation system is provided with a transducer that outputs an acoustic wave and an electro-dynamic phased array acoustic lens having an array of cells, each cell of which controls a characteristic of the acoustic wave that passes through the cell.

In accordance with a still further aspect of the invention, an acoustic ablation system includes a transducer having a plurality of transducer elements that output acoustic waves, and an electro-dynamic phased array acoustic lens having an array of cells, wherein each cell may separately control a characteristic such as, amplitude, or wave phase (for a continuous periodic wave, or, more broadly, delay, which applies also to pulsed waves) of an acoustic wave that passes through the respective cell. In preferred embodiments, the system employs feedback to determine how to control the characteristics of the acoustic waves and, in particular, to determine where to move the focal zone of the ultrasound energy, and the transducer, if necessary, relative to tissue being ablated.

In accordance with yet another aspect of the invention, there is provided a method of using an acoustic lens to control acoustic waves to ablate tissue, the method including the steps of providing an electro-dynamic phased array acoustic lens having an array of cells and separately controlling one or more characteristics of an acoustic wave that passes through each cell, such as amplitude, phase (for a continuous periodic wave) or wave front propagation delay (for a single pulse), both of these latter characteristics being broadly referred to as "delay."

In accordance with a still further aspect of the invention, there is provided a method of using an acoustic ablation system to control acoustic waves used to ablate tissue, the method including the steps of providing a transducer that outputs an acoustic wave, providing an electro-dynamic phased array acoustic lens having an array of cells, and separately controlling one or more characteristics of an acoustic wave that passes through each cell. Preferred methods further include employing feedback to determine how to control the characteristics of the acoustic waves and, in particular, to determine where to move the focus of the ultrasound energy, and the transducer, if necessary, relative to tissue being ablated.

Other aspects, advantages and features of the invention will appear hereinafter.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

This disclosure presents the design and potential applications for an electro-dynamic phased array ("EDPA") acoustic lens that may control a characteristic of an acoustic wave with a degree of control similar to or better than that of a transducer phased array.

Figure 1:
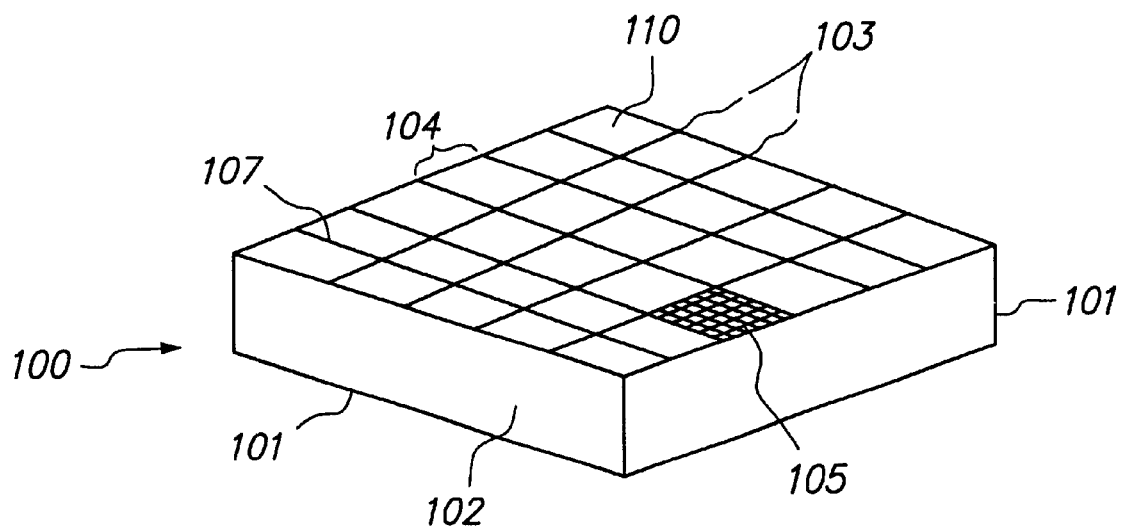
FIG. 1 is a conceptual diagram of an exemplary embodiment of an electro-dynamic phased array acoustic lens, in accordance with the present invention.

FIG. 1 is an illustration of one embodiment of an EDPA acoustic lens constructed in accordance with the present invention. The specific implementations discussed below and in reference to the figures do not explicitly exclude other embodiments or configurations.

Turning to FIG. 1, the EDPA acoustic lens 100 generally includes the following primary components: an outer support substrate 101, an internal medium 102 having voltage dependent acoustic properties, electrode surfaces (physical contacts or electrical coating) 105, 106 (shown in FIG. 2), and electrical connections 103 from the electrodes 105, 106 to voltage sources (not shown). The electrical connections 103 may be, for example, fine wires, micro-circuitry, micro-etching, or micro-lithography. Although high voltages are required, there is very low current and therefore very low power transmitted through these electrical connections. Thus, very small electrical connections are possible, as is commonly used in liquid crystal displays (LCD) such as digital watch faces. Although not directly part of the acoustic lens 100 and therefore not illustrated, a variable voltage source and a means to control the applied voltage to each element or cell 110 in the lens array 100 is also required. Likewise, a source of acoustic waves, such as a piezoelectric transducer or transducer array, would be utilized to produce and/or receive the acoustic energy transmitted through the lens 100.

The support substrate 101 is a material that has an acoustic impedance that is similar to the surrounding medium (such as water) and/or is thin in width (relative to the acoustic wavelength) to reduce the reflections and interfacial interactions of the acoustic waves that are incident on the lens, as well as a relatively low acoustic attenuation to prevent significant absorption of acoustic energy. The difference in the acoustic impedance (Z) between the substrate and the surrounding material (e.g., water) determines the amount of energy that is reflected at their interface.

Ideally, the amount of energy reflected should be close to zero for transmission through the lens. An example is to reflect less than 5–10% of the acoustical energy, although certainly this percentage may be changed as desired. The equation for the reflection (percentage) is $[(Z_2-Z_1)/(Z_2+Z_1)]^2$ where $Z_1$ and $Z_2$ are the impedances for the substrate and the surrounding material, respectively. Water has an impedance of about 1.48 MRayl. Thus, the substrate 101 may be in the range of about 0–3.0 MRayl to result in less than a 10% reflection with water. For the purposes of acoustic transmission, the substrate material 101 would have a thickness less than ¼ the wavelength of the incident wave (and ideally less than the 1/10th the wavelength) to reduce reflections. However, the thickness of the substrate 101 is not limited to these numbers and may be changed to any other desirable number for additional support (especially for substrate materials with lower acoustic impedance providing less reflection). If the substrate 101 is constructed from a thin film material (like Mylar), an additional solid frame around the perimeter of the lens may be required for physical support.

Acoustic attenuation ideally should be close to zero so that the lens material does not significantly heat up during operation and to provide as much energy transmission as possible. However, it is entirely possible that the substrate 101 may attenuate and absorb 50% or more of the incident energy without detriment to the lens. As long as the lens is not thermally damaged (warping, melting, etc.), the incident power may simply be increased to account for the lost acoustic energy transmitted. Thus, another design parameter is for the substrate 101 to have a high melting point or to withstand the thermal demands from the ultrasound energy (e.g., 0–100 Watts for 0–10 seconds). The support substrate 101 may also be positioned vertically between adjacent cells in order to isolate the medium in one cell from the medium in another cell, as well as to provide additional mechanical support. As a result, the medium in each cell may be the same medium or a different medium such that the array of cells contains a plurality of media.

Materials such as low density polyethylene, polyphenylene oxide, polystyrene, or a thin film of Mylar, for example, may be appropriate. The choice of the particular material used for the substrate 101 is a design parameter that may be selectively chosen, as understood by those skilled in the art, for the particular application and is not intended to be limited to the specific examples provided here.

The internal material or medium 102 is disposed in each cell 110 of the array of cells in lens 100 and has voltage-dependent acoustic and/or material properties. In other words, the amount of voltage applied across the medium 102 affects the acoustic properties of the medium 102. That is, by varying the voltage across the medium 102, one can change how the medium 102 affects the acoustic waves passing through the medium 102. For example, the medium 102 may be, but is not limited to, an electro-rheological (ER) fluid.

Generally, an electro-rheological fluid consists of an insulating fluid with low dielectric having a suspension of fine dielectric particles, and has the aspect that one or more of the fluid's physical properties changes in the presence of an electric field. When an electric field is applied to an electro-rheological fluid, the fluid responds by reproducibly changing one or more of its acoustic or physical properties such as the sound velocity, attenuation and/or non-linearity. These physical changes in the ER fluid are produced rapidly (on the order of microseconds) with the application of a voltage that exceeds a critical value, after which the physical changes are generally linear with increased voltage. Furthermore, the physical properties are rapidly returned to the initial baseline once the voltage potential is removed. This process may be repeated indefinitely without detriment or hysteresis to the ER fluid.

Figure 2:
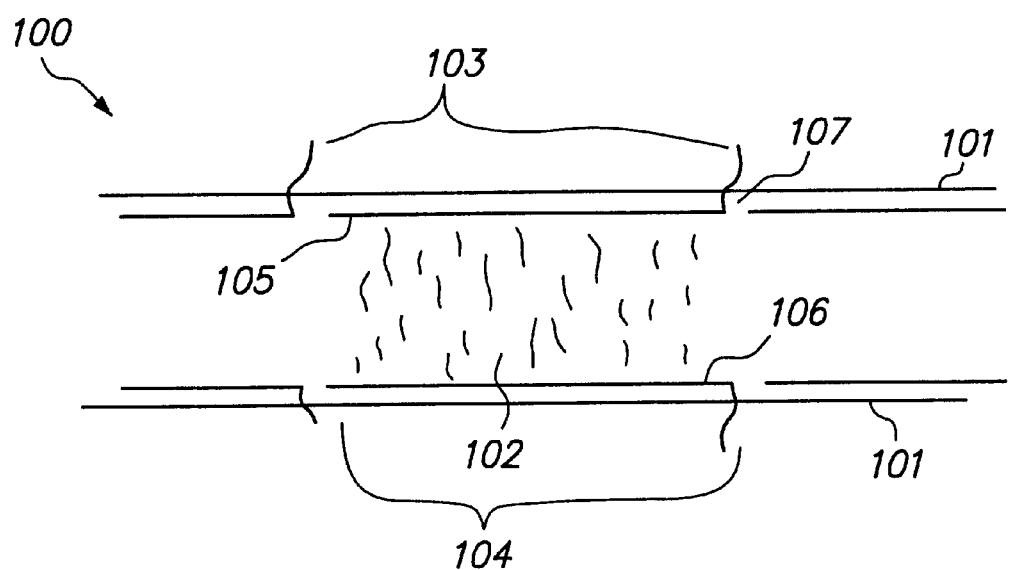
FIG. 2 is a cross-sectional view of the electro-dynamic phased array acoustic lens of FIG. 1.

One property of the electro-rheological fluid that changes with an applied electric field is the viscosity of the fluid, changing by as much as a factor of 1000. When the viscosity of the fluid changes, the bulk modulus of the fluid also changes. As seen in FIG. 2, the particulate matter shown suspended in the electro-rheological fluid tend to collect in strands and chains (thereby increasing the viscosity of the fluid) as the electric field across the fluid increases. The crystalline particulate has a modulus of elasticity that is very high and, when lined up, gives the fluid an anisotropic bulk modulus. As a result, the electro-rheological fluid has a bulk modulus that is increased in the direction of the particulate strands and chains. By controlling the voltage on the electrodes and thus the electric field across the medium, the particulate strands may be made to line up in the desired direction and change the bulk modulus.

By applying voltage to the electrodes 105, 106, the charged electrodes change the viscosity of the electro-rheological fluid so as to establish a change in the bulk modulus of the fluid that, in turn, affects the acoustic waves passing through the fluid. Thus, by controlling the electric field applied to the medium 102, one adjusts the bulk modulus and ultimately the concomitant speed of incident (and transmitted) sound waves to a desired value. The wave velocity (c) is defined by $c=(B/p)^{1/2}$, where p is the density of the medium 102, and B is the bulk modulus. The voltage applied to each cell changes the bulk modulus of the ER fluid, which, in turn changes the propagational wave velocity (or speed of sound) through the medium 102. As the bulk modulus (stiffness of the medium) increases, the acoustic wave velocity increases. As a result, the delay of the transmitted acoustic wave through each cell is controllably shifted. By controlling the wave front propagation delay or wave phase (both broadly referred to as "delay") transmitted through each cell 110, the shape, profile and/or direction of the entire acoustic beam intensity may be controlled.

Preferably, the particulate material in the electro-rheological fluid is selected to be very hard or to have a high modulus with a high dielectric constant so that the particles readily reorient themselves upon application of an electric field thereto. Thus, a preferable electro-rheological fluid would have a hard particulate phase with a relatively high acoustic impedance or high sound velocity. For example, a preferred particulate material is a piezoelectric material such as lead zirconium titanate (PZT). The fluid surrounding the particulate material is preferably a silicon based oil with a high breakdown voltage so that when voltage is applied thereto the material is not degraded or destroyed. Another example is a non-conducting fluid such as mineral oil or castor oil with a suspension of semiconducting particles such as alumino-silicate powder, $BaTiO_3$, $SrTiO_3$, $TiO_2$, $KNbO_3$, or glass beads. The particular electro-rheological fluid used is a design parameter that may be selected in accordance with the particular application in which the present invention is used and is not intended to be limited to the specific examples discussed here.

The medium 102 may also include other materials including but not limited to liquid crystal suspensions or electrolytic polymers having acoustic properties that are voltage dependent. As with the support substrate 101, the internal medium 102 should also have an acoustic impedance that is similar to the substrate and surrounding medium (which may, for example, be water) in order to minimize reflections and/or scattering as well as a relatively low acoustic attenuation to prevent excessive energy absorption and internal heating of the lens.

Accordingly, the EDPA acoustic lens 100 may actively control the transmittance of acoustic energy (i.e., the acoustic wave propagational velocity) through each element or cell 110 of the lens 110 in real-time by varying the voltage that is applied to the electrodes 105, 106 of the individual cells 110 in the lens array 100. The mechanism by which the lens 100 operates is through the use of the medium 102 that reproducibly changes its acoustic and physical properties (e.g., its bulk modulus) with the application and variation of the electric field across the medium 102.

Through individual control of the applied voltage to each cell 110 in the lens array 100, and therefore the resulting control of the acoustic properties of the lens 100, the wave front propagation delay (for pulses of acoustic energy) or the wave phase (for continuous acoustic waves) may be altered in response to the change in the propagational wave velocity as it passes through the lens 100.

The ability to shape or alter the acoustic beam pattern is 15 significantly advantageous and may be used to create desired patterns of acoustic intensity from the constructive (and destructive) interference of the acoustic waves transmitted through each cell 110 of the lens array 100. To control each cell independently, each cell 110 (or 104) has an electrical lead connection for voltage input.

Electrical connections 103 in FIGS. 1–2 show these electrical "feedlines" or voltage input connections. If each cell has both positive and negative electrodes, there may be a pair of electrical connections (one for the top electrode and another for the bottom electrode) for each cell. If there is only one ground plane, there may be an individual electrical connection for each cell (e.g., the top positive electrode) and one connection for the entire ground plane (e.g., bottom electrode). The distance between the electrode pairs, or the thickness of the active fluid medium, is significantly small, especially in relation to the surface area or size of each electrode in the cell, to prevent electrical interference between adjacent cells. In other words, each electrode pair is close enough together so that the electric field lines may be considered to be substantially straight and orthogonal to the electrode surfaces (according to the orientation of FIG. 2). Because the distance between the electrode pairs is relatively small compared to the size of the electrode and is on the order of (or smaller than) the gaps 107 between each pair of cells, the fringe effects at the edges of the cell may be considered negligible. However, even if some fringe effects are experienced, they may not substantially affect the performance of the cells.

The electrode contacts 105, 106 may be separate physical electrodes, but most practically is an electrical coating on the inside surface of the support substrate 101. When the electrode contacts 105, 106 are electrical coatings on the inside surface of the support substrate 101, small-insulated gaps 107 in the electrode coating 105, 106 may be utilized to create the size and shape of the individual electrode elements 103 in the lens array 100. The gaps 107 in the coating 105 create the boundaries for the shape of each electrode surface. An electrode surface exists everywhere there is an electrical coating 105, while the edges around the coating would form the insulated gaps 107. Within this insulated gap 107, the individual electrical feed lines to each electrode may also be created. The wires or circuitry 103 connecting each electrode 105, 106 to the voltage source may run along these insulated gaps 107. The individual electrode elements 103 may be created by pairs of positive and negative electrodes 105, 106 on the inside surfaces of the top and bottom of the support substrate 101.

Alternatively, the individual electrode elements 103 may be created by individual positive electrode elements on one side of the lens 100 with a single electrode (ground plane) covering the entire inside surface of the opposite face of the lens array 100. The shape and size of the overall lens array 100, as well as the distribution and shape of the individual cells 110, may vary depending on the intended use and application.

Figure 3:
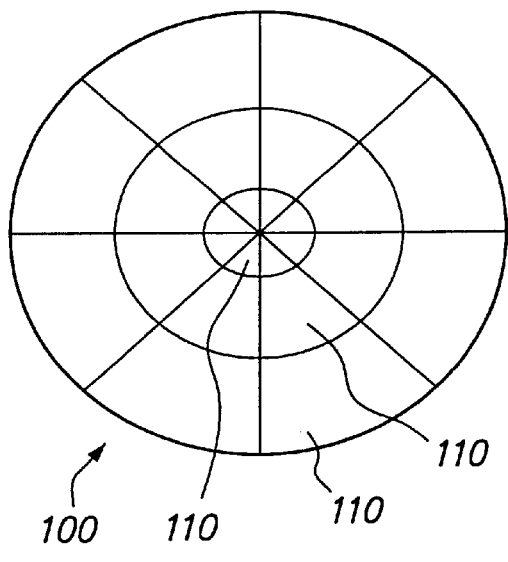
FIG. 3 is a topographical diagram illustrating the array pattern of a first embodiment of an electro-dynamic phased array acoustic lens, in accordance with the present invention.
Figure 4:
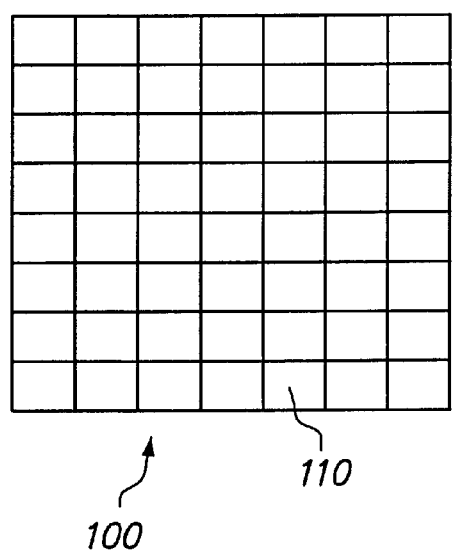
FIG. 4 is a topographical diagram illustrating the array pattern of a second embodiment of an electro-dynamic phased array acoustic lens, in accordance with the present invention.

Two examples of possible array patterns for the cells 110 of the lens 100 are shown in FIGS. 3 and 4. Although the width of the lens 100 is thin to reduce acoustic attenuation and absorption in the lens 100 itself, the lens 100 may also have a geometric focus. In FIG. 3, the cells 110 of the lens 100 may be configured into concentric circles that optionally may be divided into circumferential sectors. In FIG. 4, the cells 110 of the lens 100 may be configured into a rectangular, square, or other geometrical pattern. Each cell 110 may be separately controlled to determine a characteristic such as the delay or amplitude of the acoustic wave passing through the cell 110.

Figure 6A:
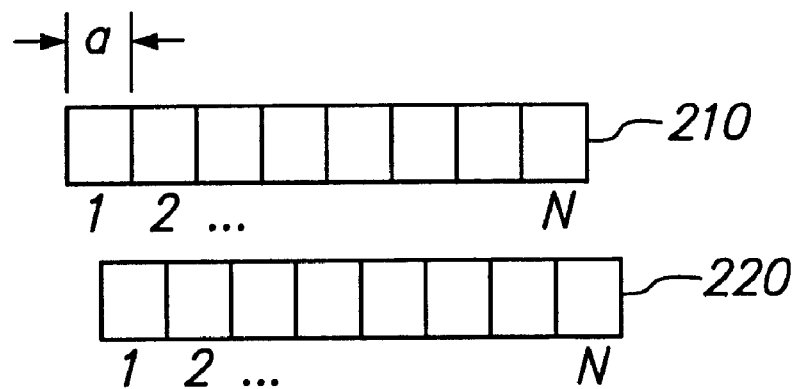
FIGS. 6A and 6B are top and side views, respectively, of a pair of electro-dynamic phased array acoustic lenses arranged to provide an increased number of effective cells.
Figure 6B:
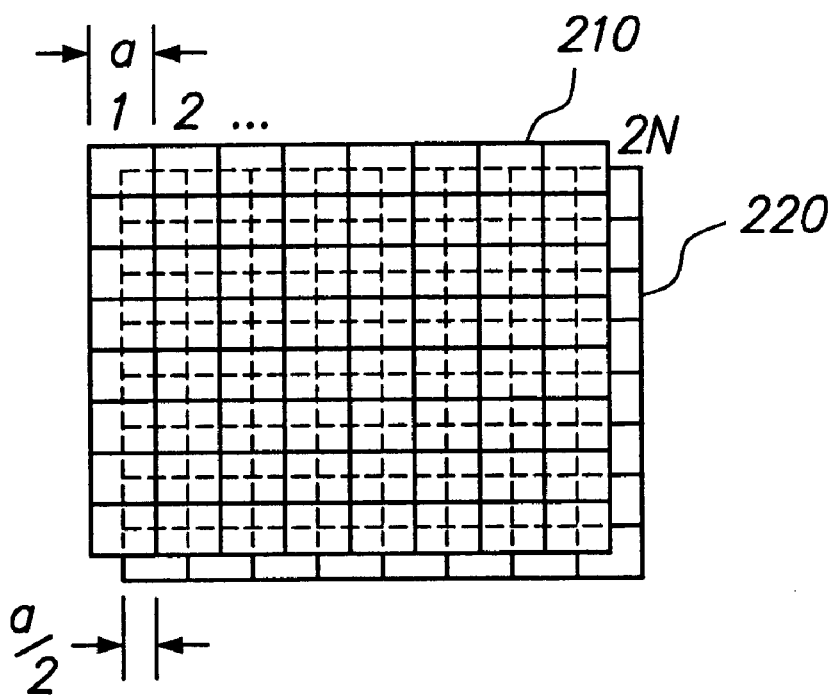

Also, a plurality of acoustic lenses may be used, overlaid on each other or adjacent to each other, for example, to create alternate patterns and/or to increase the number of cells in a given area. For example, as shown in FIGS. 6A and 6B, first and second lenses 210, 220 may be provided that are disposed substantially parallel to one another, but are shifted from a coextensive position in direct axial alignment with one another. The lenses 210, 220 are, in turn, disposed over a transducer not shown), which may be a single-element or a phased array transducer.

The lenses 210, 220 each include a substantially square array of "N" cells 212, 222 per side, each cell having a width "a." Preferably, the cells are offset from one another by half a cell dimension, i.e., by "a/2." Thus, the lenses 210, 212 effectively create a substantially square cell pattern of "2N" cells per side having widths of "a/2," thereby increasing the number of cells effectively by a factor of four (from $N^2$ to $(2N)^2$). Thus, a more numerous array of cells (for a particular size lens) may be effectively created that may be substantially easier to provide than manufacturing a single lens having a similar array of small cells. Although, a square grid of square cells is shown, other cell shapes may be used, such as triangles, hexagons, and the like, and/or other overall lens geometries and shapes may be provided that may be used to create an offset, as will be appreciated by those skilled in the art.

For example, in an alternative embodiment, the lenses may be circular and may be divided into concentric ring-shaped cells, similar to a concentric ring transducer array. The radii of the ring-shaped cells in the respective lenses may be different from one another, e.g., such that the edge of the cells on one lens are superimposed onto the middle of the cells of the other lens. In addition, the ring-shaped cells of one or both lenses may be divided further into pie-shaped sectors that may be offset circumferentially from one another. This combination of offset rings and sectors may, for example, increase the number of effective cells by a factor of four. Alternatively, one lens may be divided into ring-shaped cells and the other into pie-shaped cells. Other combinations may also be possible, as will be appreciated by those skilled in the art.

In a further alternative, a lens (or optionally multiple lenses) may be positioned over a phased array transducer, with the lens(es) and the transducer shifted from one another, similar to the two lenses described above. For example, the cells of the lens and the transducer elements of the transducer may have similar configurations, e.g., a similar grid pattern. The shifted orientation may effectively provide smaller and greater numbers of cells, than if the lens(es) and transducer were directly aligned with one another.

Many applications exist for this EDPA acoustic lens 100 because it may replace large transducer phased arrays. Significant applications exist for acoustic beam control required in medical imaging (diagnostic ultrasound), medical therapy devices (high-intensity focused ultrasound and lithotripters), and non-destructive evaluation (NDE) of various materials or products, among other possible applications. Although not limited to these applications, the EDPA lens 100 may be used to direct or focus acoustic energy to be (1) incident on a transducer operating in a reception mode (i.e., for imaging), (2) generated by a transducer operating in a production mode (i.e., for therapy), or (3) both.

Figure 5:
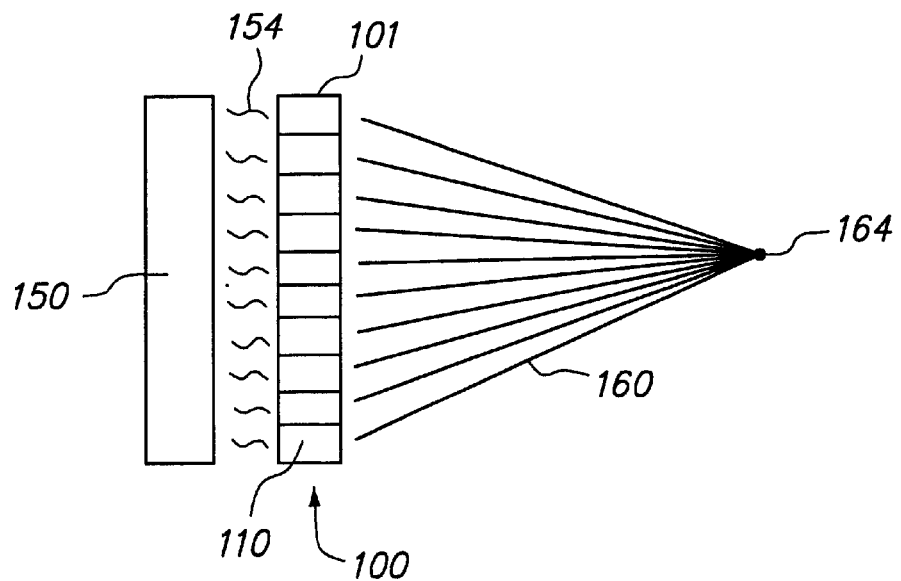
FIG. 5 is a cross-sectional view of a system having a transducer and electro-dynamic phased array acoustic lens that operate to control the focal zone of acoustic waves.

For example, for use in high-intensity focused ultrasound, the EDPA acoustic lens 100 may be used to control and direct the acoustic energy from a single-element planar transducer 150, as shown in FIG. 5. FIG. 5 illustrates a cross-sectional view of a single-element planar transducer 150 and an EDPA acoustic lens 100 working in combination. As the incident acoustic energy 154 passes through the lens array 100, the voltage to each cell 110 is controlled in order to change reproducibly the propagational wave velocity and therefore the delay of the acoustic wave passing through the cell 110. By varying the voltage to each cell 110, the transmitted acoustic waves 160 may be controlled to form a focal zone 164 of high acoustic intensity.

Further, control of the EDPA lens 100 may change the shape, size, or intensity of the focus of the acoustic waves 160, direct or steer the focal zone 164 in three-dimensional space relative to the surface of the lens 110, or produce multiple focal zones. Thus, the EDPA lens 100 operating with a single-element transducer 150 may produce the acoustic effects of a large two dimensional transducer phased array, but without the complexity and cost of such a transducer array, or the complex driving amplification circuitry and hardware required to operate the two dimensional transducer phased array.

The EDPA lens 100 would, by the application of different voltage signals, control the characteristics of the acoustic wave being applied to the tissue. For instance, one could apply and change the voltage across the medium 102 in a selected group of cells 110 out of the array of cells that comprise lens 100. Changing the voltage across the medium 102 in the selected cells would cause the medium 102 in the selected cells to alter its effect on the acoustic wave. Because the voltage (if any) across the medium 102 in the non-selected cells would not be changed, the non-selected cells would not alter their effect on the acoustic wave.

As another example, different voltages may be applied to different cells 110 in the lens 100. Consequently, each cell may affect the acoustic wave passing through it differently than another cell receiving a different voltage. By selecting cells and the voltage to be applied to the medium in the respective cells, one may control how that cell affects a characteristic of the acoustic wave passing through it. Changing characteristics of the wave, such as the amplitude and delay from each cell, allows one to controllably alter and direct the beam intensity output and focus the energy at the desired location in the tissue. In addition, the system may be used to generate a plurality of focal zones by focusing subsets of the cells in the array at different focal zones.

Moreover, the system may include a feedback element that uses the effect of the acoustic wave on the tissue to determine how the array of cells 110 should next control the characteristics of the acoustic wave. Alternatively, the system could use a feedback element to determine where to move the focus of the ultrasound energy (or if necessary, the transducer) relative to the tissue. In a preferred embodiment, the acoustic heating system with the electro-dynamic phased array lens relies on feedback and thermal images from an MRI scanner. In an alternate embodiment, the feedback element is an ultrasound source and detector to determine the relative position of the focus or intensity pattern of the transmitted energy.

While embodiments and implementations of the subject invention have been shown and described, it should be apparent that many more embodiments and implementations are within the scope of the subject invention. Accordingly, the invention is not to be restricted, except in light of the claims and their equivalents.

What is claimed is:

1. A lens for controlling a characteristic of an acoustic wave passing through the lens, comprising:
   an array of cells disposed in a plane, each cell coupled to a respective electrical connection; and
   a voltage-sensitive medium disposed in each cell, the medium having an effect on the acoustic wave that varies with a voltage applied across the medium through the respective electrical connection.

2. The lens of claim 1, wherein the respective electrical connections are configured such that differing voltages may be applied across the respective cells in the array.

3. The lens of claim 1, wherein the medium within each cell comprises a bulk modulus, the medium configured such that the bulk modulus varies with the applied voltage.

4. The lens of claim 1, wherein the medium comprises an electro-rheological fluid, a liquid crystal suspension, or an electrolytic polymer.

5. The lens of claim 1, wherein the medium comprises one or more properties, the medium configured such that the one or more properties change with the voltage applied across the medium to change a characteristic of the acoustic wave comprising its delay or amplitude.

6. The lens of claim 1, wherein the array of cells includes a support material that reduces reflection or scattering of the acoustic wave.

7. The lens of claim 6, wherein the support material has a low acoustic impedance and attenuation.

8. The lens of claim 6, wherein the support material is fabricated out of Mylar, polyethylene, polyphenylene oxide, or polystyrene.

9. The lens of claim 6, wherein the support material is positioned between each cell of the array of cells to thereby isolate the medium in the respective cells.

10. The lens of claim 1, wherein the medium includes a piezoelectric material suspended in a non-conducting or insulating fluid.

11. The lens of claim 10, wherein the piezoelectric material is lead zirconium titanate.

12. The lens of claim 10, wherein the non-conducting or insulating fluid is a silicon-based oil, mineral oil, or castor oil.

13. The lens of claim 1, wherein the medium includes alumino-silicate powder, $BaTiO_3$, $SrTiO_3$, $TiO_2$, $KnbO_3$, or glass beads suspended in a non-conducting or insulating fluid.

14. The lens of claim 1, wherein the medium is a liquid crystal suspension or electrolytic polymer.

15. The lens of claim 1, wherein the medium comprises a viscosity, the medium configured such that the viscosity changes as a voltage applied across the medium changes.

16. The lens of claim 1, wherein the lens is configured to controllably shift a delay of the acoustic wave passing through each cell in the array of cells based upon the voltage applied to provide a desired intensity pattern of the entire acoustical energy of the transmitted acoustic waves.

17. A lens for controlling one or more characteristics of an acoustic wave passing through the lens, comprising:
    a first cell containing a first voltage-sensitive medium and second cell containing a second voltage-sensitive medium, the first and second cells separated by a substrate to isolate the first and second cells from one another;
    a first electrode coupled across the first cell; and
    a second electrode coupled across the second cell;
    wherein the first and second voltage-sensitive media have an effect on the acoustic wave characteristic that varies with a voltage applied across the first and second electrodes, respectively.

18. The lens of claim 17, wherein the first medium and the second medium are the same.

19. The lens of claim 17, wherein the first medium and the second medium are different.

20. The lens of claim 17, wherein the first medium is an electro-rheological fluid having a bulk modulus, the first medium configured such that the bulk modulus changes as an electric field is applied across the fluid.

21. The lens of claim 20, wherein the first medium comprises one or more properties, the first medium configured such that the one or more properties change with the voltage applied across the medium to change one or more characteristics of the acoustic wave comprising its delay or amplitude.

22. The lens of claim 17, wherein the first and second media are configured such that a property of the first medium affects a different characteristic of the acoustic wave than does a property of the second medium.

23. The lens of claim 17, wherein the voltages applied across the first and second electrodes are independently controllable.

24. The lens of claim 17, wherein the first and second cells each include a support material that reduces reflection or scattering of the acoustic wave.

25. A system for ablating tissue, comprising:
    a transducer having one or more transducer elements configured for transmitting acoustic waves; and
    a lens positioned adjacent the transducer such that the acoustic waves transmitted by the transducer elements pass through the lens, the lens comprising:
        an array of cells disposed adjacent one another such that an incident acoustic wave from the transducer elements passes through multiple cells of the array, each cell coupled to a respective electrical circuit, and
        a voltage-sensitive medium disposed in each cell, the medium having an effect on the acoustic wave that varies with a voltage applied across the medium through the respective electrical circuit.

26. The system of claim 25, wherein the lens is offset from the transducer such that a projection of the array of cells onto the transducer elements creates an effective array of cells including a greater number of cells than are provided in the lens.

27. The system of claim 25, wherein the lens comprises first and second lenses disposed adjacent the transducer such that the one or more acoustic waves transmitted by the transducer elements pass through each of the first and second lenses, the first and second lenses including first and second arrays of cells, respectively.

28. The system of claim 27, wherein the first and second lenses are disposed adjacent one another such that the first and second arrays of cells are superimposed upon one another to create an effective array of cells including a greater number of cells than are provided in each of the first and second lenses.

29. The system of claim 27, wherein the first and second lenses are disposed in planes that are substantially parallel to one another, and wherein the first and second lenses are overlaid with respect to one another within the planes.

30. A lens for controlling a characteristic of an acoustic wave passing through the lens, comprising:
    an array of cells disposed in a plane, the array of cells comprising a substrate positioned between adjacent cells to isolate the adjacent cells from one another, each cell coupled to a respective electrical connection; and
    a voltage-sensitive medium disposed in each cell, the medium having an effect on an acoustic wave passing vertically through each respective cell that varies with a voltage applied across the medium through the respective electrical connection.

31. The lens of claim 30, wherein the array of cells are disposed in concentric circles within the plane.

32. The lens of claim 30, wherein the array of cells are disposed in a rectangular pattern within the plane.

33. A system for focusing acoustic energy, comprising:
    a transducer configured for transmitting acoustic waves towards a focal zone; and
    a lens comprising an array of cells positioned between the transducer and the focal zone, the array of cells disposed transversely with respect to the acoustic waves such that an incident acoustic wave passes through multiple cells of the array, each cell being coupled to a respective electrical circuit and including a voltage-sensitive medium therein, the medium having an effect on a portion of the acoustic wave passing through a respective cell that varies with a voltage applied across the medium through a respective electrical connection.

* * * * *